(12) United States Patent
Ladet

(10) Patent No.: US 9,987,297 B2
(45) Date of Patent: Jun. 5, 2018

(54) POLYMERIC FIBERS HAVING TISSUE REACTIVE MEMBERS

(75) Inventor: Sébastien Ladet, Lyons (FR)

(73) Assignee: Sofradim Production (FR)

( * ) Notice: Subject to any disclaimer, the term of this patent is extended or adjusted under 35 U.S.C. 154(b) by 1631 days.

(21) Appl. No.: 13/192,007

(22) Filed: Jul. 27, 2011

(65) Prior Publication Data

US 2012/0027814 A1 Feb. 2, 2012

Related U.S. Application Data

(60) Provisional application No. 61/367,964, filed on Jul. 27, 2010.

(51) Int. Cl.

| | | |
|---|---|---|
| *A61L 24/04* | (2006.01) | |
| *C07K 2/00* | (2006.01) | |
| *C07K 17/02* | (2006.01) | |
| *A61K 31/7088* | (2006.01) | |
| *A61K 38/02* | (2006.01) | |
| *A61K 31/722* | (2006.01) | |
| *C08B 37/08* | (2006.01) | |
| *A61K 38/39* | (2006.01) | |
| *C07K 14/78* | (2006.01) | |
| *A61K 31/37* | (2006.01) | |
| *C08B 3/00* | (2006.01) | |
| *A61K 31/717* | (2006.01) | |
| *A61P 17/02* | (2006.01) | |
| *A61P 41/00* | (2006.01) | |
| *A61K 31/737* | (2006.01) | |
| *A61K 31/745* | (2006.01) | |
| *A61K 31/765* | (2006.01) | |
| *A61K 31/78* | (2006.01) | |
| *A61K 31/785* | (2006.01) | |
| *A61K 31/79* | (2006.01) | |
| *A61L 17/00* | (2006.01) | |
| *A61L 24/00* | (2006.01) | |
| *A61L 31/04* | (2006.01) | |
| *A61L 31/14* | (2006.01) | |
| *D01F 11/14* | (2006.01) | |

(52) U.S. Cl.
CPC ........ *A61K 31/7088* (2013.01); *A61K 31/717* (2013.01); *A61K 31/722* (2013.01); *A61K 31/737* (2013.01); *A61K 31/745* (2013.01); *A61K 31/765* (2013.01); *A61K 31/78* (2013.01); *A61K 31/785* (2013.01); *A61K 31/79* (2013.01); *A61L 17/00* (2013.01); *A61L 24/001* (2013.01); *A61L 24/04* (2013.01); *A61L 31/04* (2013.01); *A61L 31/14* (2013.01); *D01F 11/14* (2013.01)

(58) Field of Classification Search
CPC ............ A61K 47/48215; A61K 31/425; A61K 31/655; A61K 31/4178; A61K 9/5153
USPC ..... 424/400, 178.1, 78.18, 78.24; 514/44, 1, 514/55, 17.2, 54, 57
See application file for complete search history.

(56) References Cited

U.S. PATENT DOCUMENTS

| | | |
|---|---|---|
| 3,767,085 A | 10/1973 | Cannon et al. |
| 4,326,532 A | 4/1982 | Hammar |
| 4,359,049 A | 11/1982 | Redl et al. |
| 4,464,321 A | 8/1984 | Pittalis et al. |
| 4,538,920 A | 9/1985 | Drake |
| 4,753,536 A | 6/1988 | Spehar et al. |
| 4,839,345 A | 6/1989 | Doi et al. |
| 4,857,403 A | 8/1989 | De Lucca et al. |
| 4,880,662 A | 11/1989 | Habrich et al. |
| 5,021,207 A | 6/1991 | De Lucca et al. |
| 5,372,585 A | 12/1994 | Tiefenbrun et al. |
| 5,455,308 A | 10/1995 | Bastiaansen |
| 5,562,946 A | 10/1996 | Fofonoff et al. |
| 5,578,662 A | 11/1996 | Bennett et al. |
| 5,582,955 A | 12/1996 | Keana et al. |
| 5,612,050 A | 3/1997 | Rowe et al. |
| 5,804,318 A | 9/1998 | Pinchuk et al. |
| 5,911,942 A | 6/1999 | Fofonoff et al. |
| 6,107,365 A | 8/2000 | Bertozzi et al. |
| 6,107,453 A | 8/2000 | Zuccato et al. |
| 6,312,725 B1 | 11/2001 | Wallace et al. |
| 6,342,591 B1 | 1/2002 | Zamora et al. |
| 6,451,032 B1 | 9/2002 | Ory et al. |
| 6,534,611 B1 | 3/2003 | Darling et al. |
| 6,552,103 B1 | 4/2003 | Bertozzi et al. |
| 6,570,040 B2 | 5/2003 | Saxon et al. |
| 6,576,000 B2 | 6/2003 | Carrison |
| 6,624,245 B2 | 11/2003 | Wallace et al. |
| 6,881,766 B2 | 4/2005 | Hain |
| 7,012,126 B2 | 3/2006 | Matsuda et al. |
| 7,105,629 B2 | 9/2006 | Matsuda et al. |

(Continued)

FOREIGN PATENT DOCUMENTS

| | | |
|---|---|---|
| BE | 1008260 A6 | 2/1996 |
| EP | 0490854 B1 | 9/1996 |

(Continued)

OTHER PUBLICATIONS

International Search Report and Written Opinion corresponding to International Application No. PCT/IB2011/002429, date of completion Jul. 20, 2012 and dated Aug. 1, 2012; 14 pages.

(Continued)

*Primary Examiner* — Anna Falkowitz

(57) ABSTRACT

A method for bonding a polymeric fiber to tissue is provided which includes providing a polymeric fiber having a plurality of tissue reactive members linked to a surface of the fiber via a specific binding pair, and contacting the polymeric fiber to biological tissue, to covalently bond the fiber to the tissue.

34 Claims, 2 Drawing Sheets

(56) References Cited

U.S. PATENT DOCUMENTS

| | | | |
|---|---|---|---|
| 7,122,703 B2 | 10/2006 | Saxon et al. | |
| 7,144,976 B2 | 12/2006 | Matsuda et al. | |
| 7,172,877 B2 | 2/2007 | Ting | |
| 7,247,692 B2 | 7/2007 | Laredo | |
| 7,294,357 B2 | 11/2007 | Roby | |
| 7,371,719 B2 | 5/2008 | Stupp et al. | |
| 7,375,234 B2 | 5/2008 | Sharpless et al. | |
| 7,560,588 B2 | 7/2009 | Breitenkamp et al. | |
| 7,618,944 B2 | 11/2009 | Breitenkamp et al. | |
| 7,638,558 B2 | 12/2009 | Breitenkamp et al. | |
| 7,667,012 B2 | 2/2010 | Saxon et al. | |
| 7,795,355 B2 | 9/2010 | Matyjaszewski et al. | |
| 7,807,619 B2 | 10/2010 | Bertozzi et al. | |
| 7,981,444 B2 | 7/2011 | Tomalia et al. | |
| 7,985,424 B2 | 7/2011 | Tomalia et al. | |
| 2002/0016003 A1 | 2/2002 | Saxon et al. | |
| 2002/0161170 A1 | 10/2002 | Matsuda et al. | |
| 2002/0169275 A1 | 11/2002 | Matsuda et al. | |
| 2002/0173616 A1 | 11/2002 | Matsuda et al. | |
| 2003/0100086 A1 | 5/2003 | Yao et al. | |
| 2003/0135238 A1 | 7/2003 | Milbocker | |
| 2003/0162903 A1 | 8/2003 | Day | |
| 2003/0199084 A1 | 10/2003 | Saxon et al. | |
| 2003/0205454 A1 | 11/2003 | Hlavinka et al. | |
| 2004/0170752 A1 | 9/2004 | Luthra et al. | |
| 2004/0185053 A1 | 9/2004 | Govindan | |
| 2004/0209317 A1 | 10/2004 | Ting | |
| 2005/0038472 A1 | 2/2005 | Furst | |
| 2005/0148032 A1 | 7/2005 | Saxon et al. | |
| 2005/0222427 A1 | 10/2005 | Sharpless et al. | |
| 2005/0233389 A1 | 10/2005 | Ting et al. | |
| 2006/0018948 A1 | 1/2006 | Guire et al. | |
| 2006/0036022 A1 | 2/2006 | Callaghan et al. | |
| 2006/0085033 A1 | 4/2006 | Criscuolo et al. | |
| 2006/0108393 A1 | 5/2006 | Heinrich et al. | |
| 2006/0110782 A1 | 5/2006 | Bertozzi et al. | |
| 2006/0147963 A1 | 7/2006 | Barone et al. | |
| 2006/0193865 A1 | 8/2006 | Govindan | |
| 2006/0228300 A1 | 10/2006 | Chang et al. | |
| 2006/0228357 A1 | 10/2006 | Chang et al. | |
| 2006/0240092 A1 | 10/2006 | Breitenkamp et al. | |
| 2006/0276658 A1 | 12/2006 | Saxon et al. | |
| 2007/0020620 A1 | 1/2007 | Finn et al. | |
| 2007/0037964 A1 | 2/2007 | Saxon et al. | |
| 2007/0060658 A1 | 3/2007 | Diaz et al. | |
| 2007/0077564 A1 | 4/2007 | Roitman et al. | |
| 2007/0086942 A1 | 4/2007 | Chang et al. | |
| 2007/0087001 A1 | 4/2007 | Taylor et al. | |
| 2007/0099251 A1 | 5/2007 | Zhang et al. | |
| 2007/0140966 A1 | 6/2007 | Chang et al. | |
| 2007/0178133 A1 | 8/2007 | Rolland | |
| 2007/0178448 A1 | 8/2007 | Tsao et al. | |
| 2007/0190597 A1 | 8/2007 | Agnew et al. | |
| 2007/0244265 A1 | 10/2007 | Matyjaszewski et al. | |
| 2007/0244296 A1 | 10/2007 | Tomalia et al. | |
| 2007/0249014 A1 | 10/2007 | Agnew et al. | |
| 2007/0254006 A1 | 11/2007 | Loose et al. | |
| 2007/0258889 A1 | 11/2007 | Douglas et al. | |
| 2007/0269369 A1 | 11/2007 | Gegg et al. | |
| 2007/0272122 A1 | 11/2007 | Lahann et al. | |
| 2007/0275387 A1 | 11/2007 | Ju | |
| 2007/0298006 A1 | 12/2007 | Tomalia et al. | |
| 2008/0015138 A1 | 1/2008 | Hamilton et al. | |
| 2008/0035243 A1 | 2/2008 | Breitenkamp et al. | |
| 2008/0038472 A1 | 2/2008 | Suzuki et al. | |
| 2008/0045686 A1 | 2/2008 | Meagher et al. | |
| 2008/0050731 A1 | 2/2008 | Agnew et al. | |
| 2008/0051562 A1 | 2/2008 | Chaikof et al. | |
| 2008/0121657 A1 | 5/2008 | Voegele et al. | |
| 2008/0138317 A1 | 6/2008 | Fung | |
| 2008/0160017 A1 | 7/2008 | Baker et al. | |
| 2008/0166363 A1 | 7/2008 | Govindan et al. | |
| 2008/0171067 A1 | 7/2008 | Govindan et al. | |
| 2008/0187956 A1 | 8/2008 | Carrico et al. | |
| 2008/0199736 A1 | 8/2008 | Gadeken et al. | |
| 2008/0200628 A1 | 8/2008 | Gadeken et al. | |
| 2008/0207913 A1 | 8/2008 | Breitenkamp et al. | |
| 2008/0214436 A1 | 9/2008 | Yu et al. | |
| 2008/0214801 A1 | 9/2008 | Saxon et al. | |
| 2008/0214831 A1 | 9/2008 | Sharpless et al. | |
| 2008/0221043 A1 | 9/2008 | Harth et al. | |
| 2008/0241856 A1 | 10/2008 | Wong et al. | |
| 2008/0241892 A1 | 10/2008 | Roitman et al. | |
| 2008/0242171 A1 | 10/2008 | Huang et al. | |
| 2008/0248126 A1 | 10/2008 | Cheng et al. | |
| 2008/0267878 A1 | 10/2008 | Robillard et al. | |
| 2008/0283572 A1 | 11/2008 | Boyden et al. | |
| 2008/0311412 A1 | 12/2008 | Fokin et al. | |
| 2008/0317861 A1 | 12/2008 | Guan | |
| 2009/0012457 A1 | 1/2009 | Childers et al. | |
| 2009/0018646 A1 | 1/2009 | Zhao | |
| 2009/0027603 A1 | 1/2009 | Samulski et al. | |
| 2009/0053139 A1 | 2/2009 | Shi et al. | |
| 2009/0054619 A1 | 2/2009 | Baker et al. | |
| 2009/0061010 A1 | 3/2009 | Zale et al. | |
| 2009/0069561 A1 | 3/2009 | Fokin et al. | |
| 2009/0082224 A1 | 3/2009 | Haddleton et al. | |
| 2009/0099108 A1 | 4/2009 | Jones | |
| 2009/0124534 A1 | 5/2009 | Reineke et al. | |
| 2009/0137424 A1 | 5/2009 | Tsao et al. | |
| 2009/0155335 A1 | 6/2009 | O'Shaughnessey et al. | |
| 2009/0181402 A1 | 7/2009 | Finn et al. | |
| 2009/0182151 A1 | 7/2009 | Wu et al. | |
| 2009/0202433 A1 | 8/2009 | Chang et al. | |
| 2009/0203131 A1 | 8/2009 | Reineke et al. | |
| 2009/0214755 A1 | 8/2009 | Armani et al. | |
| 2009/0220607 A1 | 9/2009 | Kiser et al. | |
| 2009/0240030 A1 | 9/2009 | Ju et al. | |
| 2009/0247651 A1 * | 10/2009 | Kapiamba et al. | 514/788 |
| 2009/0250588 A1 | 10/2009 | Robeson et al. | |
| 2009/0253609 A1 | 10/2009 | Fleury et al. | |
| 2009/0259016 A1 | 10/2009 | Johnson et al. | |
| 2009/0263468 A1 | 10/2009 | McAnulty et al. | |
| 2009/0266467 A1 * | 10/2009 | Stopek et al. | 156/60 |
| 2009/0269277 A1 | 10/2009 | Chang et al. | |
| 2009/0281250 A1 | 11/2009 | DeSimone et al. | |
| 2009/0297609 A1 | 12/2009 | Shoichet et al. | |
| 2009/0306310 A1 | 12/2009 | Wu et al. | |
| 2009/0312363 A1 | 12/2009 | Bradner et al. | |
| 2009/0325292 A1 | 12/2009 | Baker et al. | |
| 2010/0011472 A1 | 1/2010 | Hugel et al. | |
| 2010/0015046 A1 | 1/2010 | Govindan et al. | |
| 2010/0021391 A1 | 1/2010 | Douglas et al. | |
| 2010/0034862 A1 | 2/2010 | Laronde et al. | |
| 2010/0047258 A1 | 2/2010 | Wang et al. | |
| 2010/0048738 A1 | 2/2010 | Fleury et al. | |
| 2010/0069578 A1 | 3/2010 | Faust et al. | |
| 2010/0098640 A1 | 4/2010 | Cohen et al. | |
| 2010/0104589 A1 | 4/2010 | Govindan et al. | |
| 2010/0121022 A1 | 5/2010 | Musa et al. | |
| 2010/0159508 A1 | 6/2010 | Yang et al. | |
| 2010/0247433 A1 | 9/2010 | Tirrell et al. | |
| 2010/0286405 A1 | 11/2010 | Fokin et al. | |
| 2010/0291171 A1 | 11/2010 | Crescenzi et al. | |
| 2010/0303754 A1 | 12/2010 | Turpin et al. | |
| 2011/0008251 A1 | 1/2011 | Chang et al. | |
| 2011/0052696 A1 | 3/2011 | Hult et al. | |
| 2011/0060107 A1 | 3/2011 | Matyjaszewski et al. | |
| 2011/0143435 A1 | 6/2011 | Stayton et al. | |
| 2011/0177156 A1 | 7/2011 | Szoka, Jr. et al. | |
| 2011/0183417 A1 | 7/2011 | Reineke | |
| 2011/0213123 A1 | 9/2011 | Bertozzi et al. | |

FOREIGN PATENT DOCUMENTS

| | | | |
|---|---|---|---|
| EP | 1790702 A1 | 5/2007 | |
| EP | 1795563 A1 | 6/2007 | |
| EP | 1897500 * | 8/2007 | A61B 17/06 |
| EP | 1975230 A1 | 1/2008 | |
| EP | 1 897 500 A1 | 3/2008 | |
| EP | 2014308 A2 | 1/2009 | |
| EP | 2090592 A1 | 8/2009 | |
| WO | WO 01/76594 | 10/2001 | |
| WO | WO 2006/012569 A1 | 2/2006 | |

(56) References Cited

FOREIGN PATENT DOCUMENTS

| WO | WO 2007/003054 A1 | 1/2007 |
|---|---|---|
| WO | WO 2007/011696 A2 | 1/2007 |
| WO | WO 2007/041394 A2 | 4/2007 |
| WO | WO 2007/121055 A1 | 10/2007 |
| WO | WO 2008/013618 A1 | 1/2008 |
| WO | WO 2008/075955 A2 | 6/2008 |
| WO | WO 2008/077406 A2 | 7/2008 |
| WO | WO 2008/108736 A1 | 9/2008 |
| WO | WO 2008/115694 A2 | 9/2008 |
| WO | WO 2008/120016 A1 | 10/2008 |
| WO | WO 2010/040187 A1 | 4/2010 |
| WO | WO 2010/057080 A1 | 5/2010 |
| WO | 2010095052 A2 | 8/2010 |
| WO | 2010095058 A2 | 8/2010 |
| WO | WO 2010/095044 A2 | 8/2010 |
| WO | WO 2010/095049 A1 | 8/2010 |
| WO | WO 2010/095052 A2 | 8/2010 |
| WO | WO 2010/095058 A2 | 8/2010 |
| WO | 2012001532 A2 | 1/2012 |
| WO | WO 2012/001532 A2 | 1/2012 |

OTHER PUBLICATIONS

Shi, et al., "The Immobilization of Proteins on Biodegradable Polymer Fibers via Click Chemistry", Science Direct, Biomaterials, vol. 29, No. 8, Nov. 26, 2007; pp. 1118-1126.
Binder, et al. "Click Chemistry in Polymer Science: An Update", Macromolecular Rapid Communications, vol. 29, No. 12-13, Jun. 4, 2008; pp. 952-981.
Q. Shi, et al., "The Immobilization of Proteins on Biodegradable Polymer Fibers via Click Chemistry", Biomaterials, 29, (2008), pp. 1118-1126.
Jérôme, et al., "Recent Advances in the Synthesis of Aliphatic Polyesters Ring-Opening Polymerization", Advanced Drug Delivery Reviews, 60, (2008), pp. 1056-1076.
Zhang, et al., "2-Azido-2-deoxycellulose: Synthesis and 1, 3-Dipolar Cycloaddition", Helvetica Chimica Acta, vol. 91, pp. 608-617 (2008).
R. Riva, et al., "Contribution of "Click Chemistry" to the Synthesis of Antimicrobial Aliphatic Copolyester", Polymer 49, (2008), pp. 2023-2028.
Baskin, et al., "Copper Free Click Chemistry for Dynamic In Vivo Imaging", PNAS, vol. 104, No. 43, (Oct. 23, 2007), pp. 16793-16797.
Codelli, et al., "Second Generation Difluorinated Cyclooctynes for Copper-Free Click Chemistry", J. Am. Chem. Soc., vol. 130, No. 34, (2008), pp. 11486-11493.
Sletten and Bertozzi, "A Hydrophilic Azacyclooctyne for Cu-free Click Chemistry", Org. Lett. (2008) 10(14), pp. 3097-3099.
Cazalis, et al., "C-Terminal Site-Specific PEGylation of a Truncated Thrombomodulin Mutant with Retention of Full Bioactivity", Bioconjugate Chem., (2004), 15, pp. 1005-1009.
Haridas, et al., "Design and Synthesis of Triazole-based Peptidedendrimers" Tetrahedron Letters, vol. 48, (2007), pp. 4719-4722.
Raghavan, et al., "Chemical Probes for Profiling Fatty Acid-associated Proteins in Living Cells", Bioorg. Med. Chem. Lett., 18 (2008), pp. 5982-5986.
LeDévédec, et al., "Separation of Chitosan Oligomers by Immobilized Metal Affinity Chromatography", Journal of Chromatography A., 2008, 1194(2), pp. 165-171.
Hartgerink, et al., "Peptide-amphiphile Nanofibers: A Versatile Scaffold for the Preparation of Self Assembling Materials", PNAS, 2002; 99(2), pp. 5133-5138.
Van Berkel, et al., "Metal-Free Triazole Formation as a Tool for Bioconjugation" Chem Bio Chem, 8, (2007), pp. 1504-1508.
Nottelet, et al., Synthesis of an X-ray opaque biodegradable copolyester by chemical modification of poly (ε-caprolactone) Biomaterials, 27, (2006), pp. 4943-4954.

Smith, et al., "Synthesis and Convenient Functionalization of Azide-labeled Diacyglycerol Analogues for Modular Access to Biologically Active Lipid Probes", Bioconjugate Chem, 19(9), (2008). pp. 1855-1863.
Skierka, et al., "The Influence of Different Acids and Pepsin on the Extractability of Collagen From the Skin of Baltic Cod (*Gadus morhua*)", Food Chemisty, 105, (2007), pp. 1302-1306.
Eastoe, "The Amino Acid Composition of Mammalian Collagen and Gelatin", vol. 61, (1955), pp. 589-600.
Sicherl, et al., "Orthogonally Protected Sugar Diamino Acids as Building Blocks for Linear and Branched Oligosaccharide Mimetics", Angew. Chem. Int. Ed. 44, (2005), pp. 2096-2099.
Laughlin, et al., "In Vivo Imaging of Membrane-Associated Glycans in Developing Zebrafish", Science, 320, (2008), pp. 664-667.
Worch and Wittmann, "Unexpected Formation of Complex Bridged Tetrazoles via Intramolecular 1,3-dipolar Cycloaddition of 1,2-0-cyanoalkylidene Derivatives of 3-azido-3-deoxy-D-allose", Carbohydrate Research, 343, (2008), pp. 2118-2129.
Witczak et al., "A Click Chemistry Approach to Glycomimetics: Michael addition of 2,3,4,6-tetra-O-acetyl-1-thio-β-D-glucopyranose to 4-deoxy-1,2-O-isopropylident-L-*glycero*-pent-4-enopyranos-3-ulose-a convenient route to novel 4-deoxy-(1→5)-5-C-thiodisaccharides", Carbohydrate Research, 342, (2007), 1929-1933
Marra, et al., "Validation of the Copper(1)-Catalyzed Azide-Alkyne Coupling in Ionic Liquids, Synthesis of a Triazole-Linked C-Disaccharide as a Case Study", J. Org. Chem (2008), 73(6), pp. 2458-2461.
Srinivasachari, et al., "Versatile Supramolecular pDNA Vehicles via "Click Polymerization" of β-cyclodextrin with oligoethyleneamines", Biomaterials, 30, (2009), pp. 928-938.
Arora, et al., "A Novel domino-click approach for the synthesis of sugar based unsymmetrical bis-1,2,3-triazoles", Carbohydrate Research, 343, (2008), 139-144.
Chen, et al., "Synthesis of a $C_3$-symmetric (1→6)-N-acetyl-β-D-glucosamine Octadecasaccharide using Click Chemistry", Carbohydrate Research, 340, (2005), pp. 2476-2482.
Gouin, et al., "Multi-Mannosides Based on a Carbohydrate Scaffold: Synthesis, Force Field Development, Molecular Dynamics Studies, and Binding Affinities for Lectin Con A", J. Org. Chem., 2007, 72(24), pp. 9032-9045.
Srinivasachari, Etal., "Effects of Trehalose Click Polymer Length on pDNA Complex Stability and Delivery Efficacy", Biomaterials, 28, (2007), pp. 2885-2898.
Godeau, et al., Lipid-Conjugated Oligonucleotides via "Click Chemistry" Efficiently Inhibit Hepatitis C Virus Translation, J. med. Chem., 2008, 51(15), pp. 2374-4376.
Zou et al., "Cu-free Cycloaddition for Identifying Catalytic Active Adenylation Domains of Nonribosomal Peptide Synthesis by phage display", Bioorganic & Medicinal Chemistry Letters, 18 (2008), pp. 5664-5667.
Cantel, et al., "Synthesis and Conformational Analysis of a Cyclic Peptide Obtained via i to i + 4 Intramolecular Side-chain to Side-chain Azide-Alkyne 1,3-Dipolar Cycloaddition" J. Org. Chem., 2008, 73 (15), pp. 5663-5614.
Dijk, et al., "Synthesis of Peptide-Based Polymers by Microwave-Assisted Cycloaddition Backbone Polymerization," Biomacro molecules, 2007, 8(2), pp. 327-330.
Köster, et al., "Spectroscopic and Electrochemical Studies of Ferroceryl Triazole Amino Acid and Peptide Bioconjugates Synthesized by Click Chemistry", Organometallics, 2008, 27(23) pp. 6326-6332.
Dijk, et al., "Synthesis and Characterization of Biodegradable Peptide-Baed Polymers Prepared by Microwave-Assisted Click Chemisty", Biomacromolecules, 2008, 9(10), pp. 2834-2843.
Jiang, et al., "Amphiphilic PEG/alkyl-grafted comb polylactides", J. Polymer Science Part B: Polymer Physics, 45(22), 2007, pp. 5227-5236.
Ochs, et al., "Low-Fouling, Biofunctionalized, and Biodegradable Click Capsules", Biomacromolecules, 2008, 9(12), pp. 3389-3396.

(56) References Cited

OTHER PUBLICATIONS

Beatty and Tirrell, "Two-color Labeling of Temporally Defined Protein Populations in Mammalian Cells", Bioorg. Med. Chem. Lett., 18 (2008), pp. 5995-5999.
Kolb, et al., "Click Chemistry: Diverse Chemical Function from a Few Good Reactions", Angewandte Chemie, International Edition, Jun. 2001, pp. 2004-2021.
Krouit, et al., "Cellulose surface grafting with polycaprolactone by heterogeneous click-chemistry", European Polymer Journal 44, Dec. 2008, pp. 4074-4081.
Nandivada, et al. "Reactive polymer coatings that 'Click'.", Angewandte Chemie, International Edition 45, Apr. 2006, pp. 3360-3363.
Ossipov and Hilborn, "Poly(vinyl alcohol)-Based Hydrogels Formed by Click Chemistry", Macromelecules 2006, 39, pp. 1709-1718.
Binder and Sachsenhofer, "Click Chemistry in Polymer and Materials Science", Macromolecular Rapid Commun. 2007, 28, pp. 15-54.
Australian Examination Report, Application No. 2011284449 dated Jan. 7, 2015.
Canadian Office Action dated Jul. 10, 2017 in corresponding Canadian Patent Application No. 2,805,987, 3 pages.

* cited by examiner

POLYMERIC FIBERS HAVING TISSUE REACTIVE MEMBERS

CROSS-REFERENCE TO RELATED APPLICATION

The present application claims the benefit of and priority to U.S. Provisional Application Ser. No. 61/367,964, filed on Jul. 27, 2010, the entire disclosure of which is incorporated herein by reference.

BACKGROUND

1. Technical Field

The present disclosure relates to polymeric fibers having tissue reactive members and methods of bonding such polymeric fibers to biological tissues.

2. Related Art

Techniques for repairing damaged or diseased tissue are widespread in medicine. Wound closure devices such as sutures, staples and other repair devices such as mesh or patch reinforcements are frequently used for repair. For example, in the case of hernias, techniques involving the use of a mesh or patch to reinforce the abdominal wall are being used. The mesh or patch can generally be held in place by suturing or stapling to the surrounding tissue. Unfortunately, the use of such sutures or staples may increase the patient's discomfort and, in certain instances, there may be a risk of weakening thin or delicate tissue when the sutures or staples are knotted or deformed.

Click chemistry is a popular term for reliable reactions that make it possible for certain chemical building blocks to "click" together and form an irreversible linkage. See, e.g., U.S. Pub. No. 2005/0222427. Since its recent introduction, click chemistry has been used for ligation in biological and medical technology. In the case of azide-alkyne click chemistry, the reactions may be catalyzed or uncatalyzed. For example, copper-free click chemistry was recently developed by Bertozzi and colleagues using difluorinated cyclooctyne or DIFO, that reacts with azides rapidly at physiological temperatures without the need for a toxic catalyst. See, e.g., Baskin et al., Copper Free Click Chemistry for Dynamic In Vivo Imaging, PNAS, vol. 104, no. 43, 16793-16797 (Oct. 23, 2007). The critical reagent, a substituted cyclooctyne, possesses ring strain and electron-withdrawing fluorine substituents that together promote a [3+2] dipolar cycloaddition with azides. See also, U.S. Pub. No. 2006/0110782 and Codelli et al., Second Generation Difluorinated Cyclooctynes for Copper-Free Click Chemistry, J. Am. Chem. Soc., vol. 130, no. 34, 11486-11493 (2008). Another suitable cyclooctyne is 6,7-dimethoxyaza-cyclooct-4-yne (DIMAC). See, Sletton and Bertozzi, A hydrophilic azacyclooctyne for Cu-free click chemistry, Org. Lett. (2008) 10 (14), 3097-3099. Other click chemistry reactions include Diels-Alder reactions, thiol-alkene reactions, and maleimide-thiol reactions. There is a continuing need to generate improvements in tissue repair technology and advance the state of the art.

SUMMARY

Figure 1:
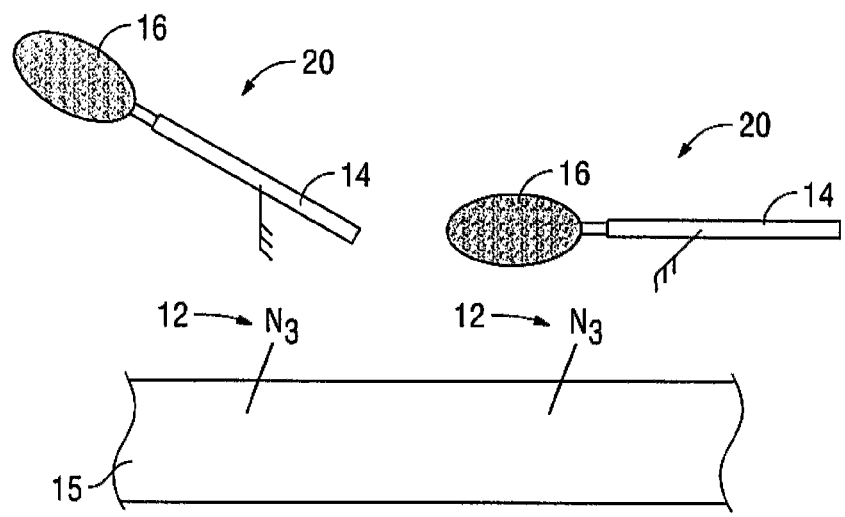
FIG. 1 schematically illustrates a fiber prior to attachment of a linking member in accordance with an embodiment described herein.

The present disclosure describes a polymeric fiber including a surface having a plurality of surface reactive members of a specific binding pair, and a plurality of linking members, each linking member including at least one complimentary surface reactive member of the specific binding pair, and at least one tissue reactive member, wherein the surface reactive members and the complementary surface reactive members are covalently bonded, adhering the tissue reactive members to the surface of the fiber.

A method for bonding a polymeric fiber to biological tissue is also provided which includes: providing a polymeric fiber having a plurality of surface reactive members of a specific binding pair attached on a surface of the fiber; attaching a plurality of linking members to the surface of the polymeric fiber, each linking member having at least one complimentary surface reactive member of the specific binding pair to attach the linking member to the surface of the polymeric fiber and at least one tissue reactive member; and, contacting the polymeric fiber with the biological tissue, wherein upon contact of the tissue reactive members on the surface of the polymeric fiber with the biological tissue, covalent bonds are formed between the tissue reactive members and the biological tissue, thus adhering the polymeric fiber to the biological tissue.

DETAILED DESCRIPTION

A surgical bonding system is provided in which fibers or filaments having pendant tissue reactive members covalently bond to biological tissue to close or seal a wound. The tissue reactive members may be attached to any portion of the fiber surface via a plurality of linking members. Each linking member includes at least one tissue reactive member and at least one complimentary surface reactive member of a specific binding pair. Prior to attachment of the linking member to the fiber, the fiber surface includes at least one surface reactive member of a specific binding pair, to which the complimentary surface reactive member of the linking member may covalently attach to the fiber. Once the linking member is attached to the fiber, a pendant tissue reactive member is positioned on the fiber for interaction with the biological tissue upon implantation.

In embodiments, the surface reactive members and the complimentary surface active members of a specific binding pair bind to one another via click chemistry. Click chemistry refers to a collection of surface reactive members having a high chemical potential energy capable of producing highly selective, high yield reactions. The surface reactive members react to form extremely reliable molecular connections in most solvents, including physiologic fluids, and often do not interfere with other reagents and reactions. Examples of click chemistry reactions include Huisgen cycloaddition, Diels-Alder reactions, thiol-alkene reactions, and maleimide-thiol reactions.

Huisgen cycloaddition is the reaction of a dipolarophile with a 1,3-dipolar compound that leads to 5-membered (hetero)cycles. Examples of dipolarophiles are alkenes and alkynes and molecules that possess related heteroatom functional groups (such as carbonyls and nitriles). 1,3-Dipolar compounds contain one or more heteroatoms and can be described as having at least one mesomeric structure that represents a charged dipole. They include nitril oxides, azides, and diazoalkanes. Metal catalyzed click chemistry is an extremely efficient variant of the Huisgen 1,3-dipolar cycloaddition reaction between alkyl-aryly-sulfonyl azides, C—N triple bonds and C—C triple bonds which is well-suited herein. The results of these reactions are 1,2 oxazoles, 1,2,3 triazoles or tetrazoles. For example, 1,2,3 triazoles are formed by a copper catalyzed Huisgen reaction between alkynes and alkyl/aryl azides. Metal catalyzed Huisgen reactions proceed at ambient temperature, are not sensitive to solvents, i.e., nonpolar, polar, semipolar, and are highly tolerant of functional groups. Non-metal Huisgen reactions (also referred to as strain promoted cycloaddition) involving use of a substituted cyclooctyne, which possesses ring strain and electron-withdrawing substituents such as fluorine, that together promote a [3+2] dipolar cycloaddition with azides are especially well-suited for use herein due to low toxicity as compared to the metal catalyzed reactions. Examples include DIFO and DIMAC. Reaction of the alkynes and azides is very specific and essentially inert against the chemical environment of biological tissues. One reaction scheme may be represented as:

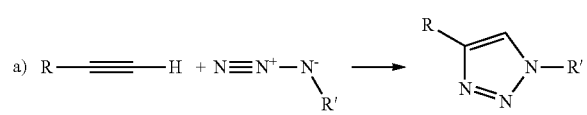

where R and R' are a polymeric material or a component of a biologic tissue.

The Diels-Alder reaction combines a diene (a molecule with two alternating double bonds) and a dienophile (an alkene) to make rings and bicyclic compounds. Examples include:

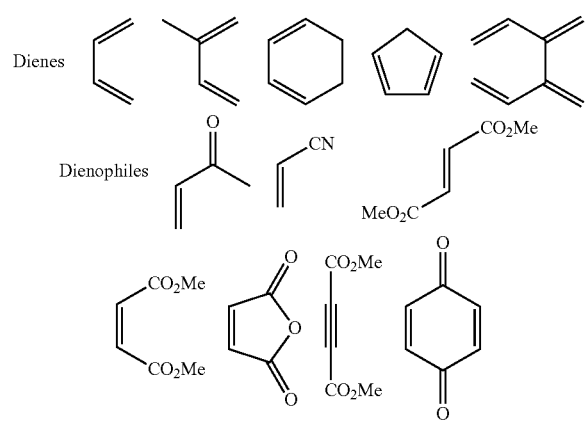

The thiol-alkene (thiol-ene) reaction is a hydrothiolation, i.e., addition of RS—H across a C=C bond. The thiol-ene reaction proceeds via a free-radical chain mechanism. Initiation occurs by radical formation upon UV excitation of a photoinitiator or the thiol itself. Thiol-ene systems form ground state charge transfer complexes and therefore photopolymerize even in the absence of initiators in reasonable polymerization times. However, the addition of UV light increases the speed at which the reaction proceeds. The wavelength of the light can be modulated as needed, depending upon the size and nature of the constituents attached to the thiol or alkene. A general thiol-ene coupling reaction mechanism is represented below:

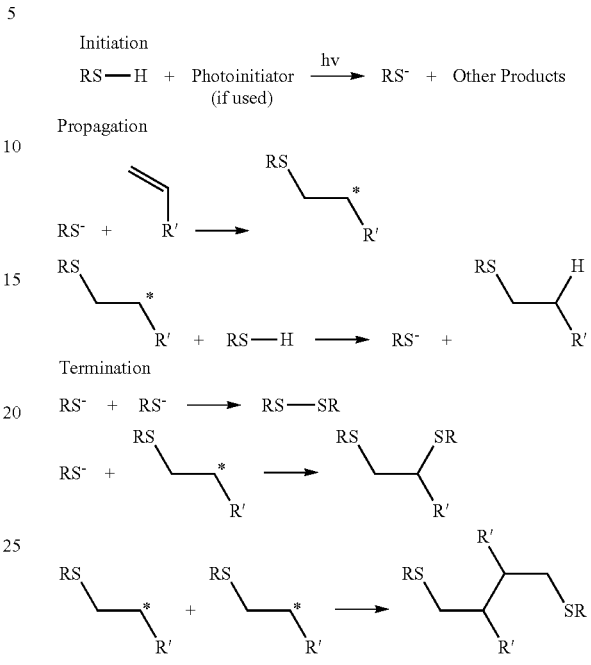

In accordance with the disclosure herein, a polymeric fiber, such as a surgical suture, is provided with a plurality of surface reactive members of a specific binding pair attached on the surface of the fiber. When the surface reactive members of the fiber are contacted with a linking member containing complementary surface reactive members of the specific binding pair, covalent attachment occurs, thus adhering the linking member to the fiber. In embodiments, the surface reactive members may be a dipolarophile or a 1,3 dipolar compound depending on which complement is applied to the linking member or the fiber. For example, if a dipolarphile is located on the fiber, the 1,3 dipolar compound will be located on the linking member. If a dipolarphile is located on the linking member, the 1,3 dipolar compound will be located on the fiber. In embodiments, the Diels-Alder members of a specific binding pair may be either a diene and a dienophile depending on which complement is applied to the linking member or the fiber. For example, if a diene is located on the fiber, the dienophile can be located on the linking member. If a diene is located on the linking member, the dienophile can be located on the fiber. In embodiments, the thiol-ene members of a specific binding pair may be either a thiol and an alkene depending on which complement is applied to the linking member or the fiber. For example, if a thiol is located on the fiber, the alkene can be located on linking member. If a thiol is located on the linking member, the alkene can be located on the fiber.

The polymeric fiber and the linking member may be constructed from any biocompatible absorbable polymer or biocompatible non-absorbable polymer. Examples of suitable polymers include polycarbonates, polyolefins, polymethacrylates, polystyrenes, polyamides, polyurethanes, polyethylene terephthalate, poly (lactic acid), poly (glycolic acid), poly (hydroxybutyrate), dioxanones (e.g., 1,4-dioxanone), δ-valerolactone, 1,dioxepanones (e.g., 1,4- dioxepan-2-one and 1,5-dioxepan-2-one), poly (phosphazine), polyesters, polyethylene glycol, polyethylene oxides, polyacrylamides, cellulose esters, fluoropolymers, vinyl polymers, silk, collagen, alginate, chitin, chitosan, hyaluronic acid, chondroitin sulfate, glycosaminoglycans, polyhydroxyethylmethylacrylate, polyvinylpyrrolidone, polyvinyl alcohol, polyacrylic acid, polyacetate, polycaprolactone, polypropylene, glycerols, poly(amino acids), copoly (ether-esters), polyalkylene oxalates, polyamides, poly (iminocarbonates), polyalkylene oxalates, polyoxaesters, polyorthoesters, polyphosphazenes, polypeptides and copolymers, block copolymers, homoploymers, blends and combinations thereof.

In the present application, the term "bioresorbable" and "bioabsorbable" are used interchangeably and are intended to mean the characteristic according to which an implant and/or a material is resorbed by the biological tissues and the surrounding fluids and disappears in vivo after a given period of time, that may vary, for example, from one day to several months, depending on the chemical nature of the implant and/or of the material. Non bioresorbable material—also called permanent material—is not substantially resorbed by tissues and surrounding fluids, after 2 years and more, keeping in particular most (e.g., >80%) of their mechanical properties after such a time. The term "biocompatible" is intended to mean the characteristic according to which an implant and/or a material is well integrated by the biological tissues and the surrounding fluids without inducing excessive inflammation reaction around the bulk of the material or due to its degradation. The material should avoid also the formation of a fibrous capsule which usually results in the delay of the cellular integration of a porous implant.

Many of the above described examples of polymers do not contain functional groups in their molecules. In embodiments, the surface reactive members and complimentary surface reactive members are attached to the polymeric fiber or linking member by surface modification techniques such as plasma treatment, silane coupling treatment and acid sensitization. Surface activation of the fiber or linking member can be achieved by acid or base hydrolysis, treatment by means of cold plasma, by chemical reactions or electromagnetic radiations.

Hydrolysis can be conducted in the presence of an aqueous solution of a base or an acid to accelerate surface reaction, inasmuch as excessively long processes of activation can induce a reduction in molecular weight and thus in the mechanical properties of the material. Suitable bases for obtaining watery solutions suited to the aim are, for example, strong alkalis, such as LiOH, $Ba(OH)_2$, $Mg(OH)_2$, NaOH, KOH, $Na_2CO_3$, $Ca(OH)_2$ and the weak bases, such as for example $NH_4OH$ and the amines such as methylamine, ethylamine, diethylamine and dimethylamine. Acids suitable for surface hydrolysis treatments can be chosen, for example, from among HCl, $HClO_3$, $HClO_4$, $H_2SO_3$, $H_2SO_4$, $H_3PO_3$, $H_3PO_4$, HI, $HIO_3$, HBr, lactic acid, glycolic acid. Surface activation by means of hydrolysis can be conducted at temperatures preferably comprised between 0 degrees Celsius and the material softening temperature.

Plasma treatment can be carried out both in the presence of a reactive gas, for example air, Ar, $O_2$ with the formation of surface activation of oxygenate type, such as —OH, —CHO, —COOH.

Surface treatment, whether hydrolytic or with plasma, can remain unaltered or can be followed by further chemical modifications to provide the first reactive groups on the bioabsorbable polymeric surface. Thus, for example, the COONa groups generated by a base hydrolysis can be subsequently converted into COOH groups by treatment with strong mineral acids. Further, the surface freeing of alcoholic groups by means of a hydrolysis process can be followed by reaction by means of the addition of a compound provided with functional group or groups able to react with surface alcoholic groups, such as for example by means of the addition of an anhydride such as succinic anhydride, with the conversion of —OH groups into —O—CO—CH2-CH2-COOH groups. Suitable surface activation techniques are disclosed in U.S. Pat. No. 6,107,453, the entire disclosure of which is incorporated herein by this reference.

During manufacture of the polymeric fiber or linking member, pendant functional groups can be incorporated into the polymer backbone by, e.g., copolymerization with functionalized monomer such as lactones, cyclic carbonates and morpholine-2,5-diones. The azido group, $N_3$ is a nucleophilic group that will exchange with other nucleophilic groups, e.g., —OH, —$NH_2$ and halogens (Br, Cl, or I). For example, 1,3-dipolar compounds may be conjugated to aliphatic polyesters, by copolymerizing ε-caprolactone and α-chloro-ε-caprolactone and then substituting an azide group for the Cl atom. Polyesters can incorporate pendant dipolarophiles, e.g., propargyl groups, by copolymerization of ε-caprolactone and α-propargyl-δ-valerolactone. Copolymers of L-lactide containing propargyl groups may, e.g., be prepared by ring opening copolymerization of 5-methyl-5-propargyloxycarbonyl-1,3-dioxanone with L-lactide at a molar ratio of about 90:10 with $ZnEt_2$ as a catalyst. See, Shi et al., Biomaterials, 29 (2008) 1118-1126. Azide functionalized polystyrene is synthesized using atom transfer radical polymerization and subsequent modification with azidotrimethylsilane and tetrabutylammonium fluoride. See, Dirks, et al., Chem. Comm., (2005) 4172-4174. Azides may be incorporated onto methacrylates, e.g., 3 azidopropyl methacrylate which is copolymerized to a block copolymer. Diels-Alder functionalities and thiol-ene functionalities are likewise incorporated into polymers herein.

In embodiments, the polymeric fiber may be a surgical suture. In some embodiments, the fiber may be a monofilament or a multifilament. In embodiments, the polymeric fiber may include at least one barb. In still other embodiments, the polymeric fiber may be used to form fibrous medical devices. Some non-limiting examples of such fibrous medical devices include sutures, staples, clips, patches and meshes.

The medical device may be selected from any conventional implantable fibrous device suitable for use in tissue reinforcement, e.g., hernia repair, or as an anti-adhesion barrier, hemostatic patch, bandages, pledgets, buttreses and the like. Any of the biocompatible polymers listed above may be utilized.

Indeed, the polymeric fibers described herein, as well as any fibrous medical device, may be formed using any techniques known to those skilled in the art, such as knitting, weaving, braiding, tatting, nonwoven techniques, freeze drying, solvent casting, extruding, molding, spinning, and the like. It is envisioned that the fibers may be formed from any permanent biocompatible materials (e.g. polyesters, polypropylene), biodegradable biocompatible materials (e.g. polylactic acid, polyglycolic acid, oxidized cellulose, and chitosan) or with a combination at any proportion of both permanent and biodegradable materials.

The surface of the polymeric fiber or device includes at least one surface reactive member before the linking member is attached to the fiber. The linking member is provided with at least one complimentary surface reactive member to interact with the surface reactive member of the fiber to form a covalent bond between the fiber and the linking member. The linking member also includes a tissue reactive member which remains capable of interacting with the biological tissue when implanted.

In embodiments, a linking member may be a polymeric material made from any of the suitable polymeric materials described herein. Like some polymeric fibers, the linking member may naturally include the complimentary surface reactive members, however in some embodiments, the linking members may require the addition or attachment of the complimentary surface reactive member. Similarly, the linking member may naturally include the tissue reactive members or the linking members may require the addition or attachment of the tissue reactive members.

The tissue reactive members are functional groups or other molecular segments that react with electrophilic or nucleophilic moieties present at the tissue site, e.g., amino and sulfhydryl groups on peptides, proteins, cell surfaces, and extracellular matrix components, to form covalent bonds. Generally, and as will be appreciated by those skilled in the art, the moieties at the tissue site are nucleophilic. Thus, in certain embodiments, the tissue reactive members may be electrophilic.

The term "nucleophilic" refers to a functional member that is electron rich, has an unshared pair of electrons acting as a reactive site, and reacts with a positively charged or electron-deficient site, generally present on another molecule. The term "nucleophile" refers to a compound having a nucleophilic site.

The term "electrophilic" refers to a functional member that is susceptible to nucleophilic attack, i.e., susceptible to reaction with an incoming nucleophilic member. Electrophilic members herein are typically electron-deficient. The term "electrophile" refers to a compound having an electrophilic site. General examples of electrophilic reactive members include (1) alkenyloxycarbonyl groups, i.e., carboxylic acid esters, and "activated" esters; (2) halocarbonyl groups such as acid chloride groups (—CO—Cl); (3) anhydrides (—(CO)—O—(CO)—R, where R is substituted or unsubstituted alkyl, aryl, alkaryl, etc.); (4) acyl groups (ketones) and formyl groups (aldehydes), including α,β-unsaturated ketones and aldehydes (e.g., —CH═CH—CH═O and —CH═CH—C(CH$_3$)═O); (5) halides, particularly chloro substituents; (6) isocyano groups (—N═C═O); (7) isothiocyano groups (—N═C═S); (8) epoxides; (9) activated hydroxyl groups (e.g., activated with conventional activating agents such as carbonyldiimidazole or sulfonyl chloride); and (10) alkenyl groups, including conjugated olefins, such as ethenesulfonyl (—SO$_2$CH═CH$_2$) and analogous functional groups, including acrylate (—CO$_2$—C═CH$_2$), methacrylate (—CO$_2$—C(CH$_3$)═CH$_2$)), ethyl acrylate (—CO$_2$—C(CH$_2$CH$_3$)═CH$_2$), and ethyleneimino (—CH═CH—C═NH).

Further examples of electrophilic tissue reactive members include, without limitation: mixed anhydrides such as PEG-glutaryl-acetyl-anhydride; PEG-glutaryl-isovaleryl-anhydride; PEG-glutaryl-pivalyl-anhydride; ester derivatives of p-nitrophenol, p-nitrothiophenol, and pentafluorophenol; esters of substituted hydroxylamines such as those of N-hydroxy-phthalimide, N-hydroxy-succinimide, and N-hydroxy-glutarimide; esters of 1-hydroxybenzotriazole, 3-hydroxy-3,4-dihydrobenzotriazine-4-one and 3-hydroxy-3,4-dihydro-quinazoline-4-one; derivatives of carbonylimidazole; and isocyanates. With these compounds auxiliary reagents can also be used to facilitate bond formation. For example 1-ethyl-3-(3-dimethylaminopropyl)] carbodiimide can be used to facilitate coupling of carboxyl groups (i.e., glutarate and succinate) with sulfhydryl groups.

It is envisioned that certain tissue reactive members may be more selective to different layers or types of biological tissue. For example, the FGF (fibroblast growth factor) is a ligand selective for the fibroblast cells which may be found in connective tissues and/or the dermal layer of a human's skin. In another example, the β1 integrin is a ligand selective for the keratinocytes which may be found in the epidermal layer of skin. In some embodiments, the polymeric fibers described herein may include pendant tissue reactive members specific to certain types of cells or tissue, i.e., FGF and β1 integrin.

In other embodiments, the linking member may be a ligand suitable for reacting with biological tissue and which bears a complimentary surface reactive member suitable for interacting with the surface reactive member on the fiber. The ligand may bind naturally to a desired target on the tissue and thus provides a vehicle for transporting and directly binding the polymeric fiber to the tissue. The ligand herein is any molecule or combination of molecules which demonstrates an affinity for biological tissue or a target in the biological tissue. Examples of ligands include nucleic acid probes, antibodies, hapten conjugates, and cell adhesion peptides such as RGD. The mechanisms involved in obtaining and using such ligands are well-known. In embodiments, complimentary surface reactive members or complementary reactive members are incorporated into saccharides or polysaccharides and attached to the fiber prior to contact with cellular tissue, wherein upon contact with the tissue the polysaccharides may be metabolically incorporated into cells. See, e.g., Baskin et al., supra.

Antibodies that specifically recognize antigens are useful in accordance with one embodiment herein. Antibodies which are conjugated to a complimentary surface reactive member are utilized to bind to proteins located on tissue. Monoclonal or polyclonal antibodies are raised against an antigen which can be any component of biological tissue and then purified using conventional techniques. The term "antibody" is intended to include whole antibodies, e.g., of any isotype (IgG, IgA, IgM, IgE, etc.), and to include fragments thereof which are also specifically reactive with a vertebrate, e.g., mammalian, protein. Antibodies may be fragmented using conventional techniques and the fragments screened for utility in the same manner as for whole antibodies. Thus, the term includes segments of proteolytically-cleaved or recombinantly-prepared portions of an antibody molecule that are capable of selectively reacting with a certain protein. Non-limiting examples of such proteolytic and/or recombinant fragments include Fab, F(ab')2, Fab', Fv, and single chain antibodies (scFv) containing a V[L] and/or V[H] domain joined by a peptide linker. The scFv's may be covalently or non-covalently linked to form antibodies having two or more binding sites. The present disclosure includes polyclonal, monoclonal or other purified preparations of antibodies and recombinant antibodies.

After purification, the ligands (e.g., antibodies, nucleic acid probes, hapten conjugates and cell adhesion peptides), are conjugated or linked to surface reactive members or complementary reactive members in the manners described above. In addition, surface reactive members or complementary reactive members can be linked to ligands by cross-linking procedures which, in accordance with the present invention, do not cause denaturing or misfolding of the ligands. The terms "linked", "attached", or "conjugated" as used herein are used interchangeably and are intended to include any or all of the mechanisms known in the art for coupling the surface reactive members, complementary surface reactive members, or tissue reactive members to the ligand and/or polymer materials. For example, any chemical or enzymatic linkage known to those with skill in the art is contemplated including those which result from photoactivation and the like. Homofunctional and heterobifunctional cross linkers are all suitable. Reactive groups (distinguishable from surface reactive members or complementary surface reactive members or tissue reactive members herein) which can be cross-linked with a cross-linker include primary amines, sulfhydryls, carbonyls, carbohydrates and carboxylic acids.

Cross-linkers are conventionally available with varying lengths of spacer arms or bridges. Cross-linkers suitable for reacting with primary amines include homobifunctional cross-linkers such as imidoesters and N-hydroxysuccinimidyl (NHS) esters. Examples of imidoester cross-linkers include dimethyladipimidate, dimethylpimelimidate, and dimethylsuberimidate. Examples of NHS-ester cross-linkers include disuccinimidyl glutamate, disucciniminidyl suberate and bis(sulfosuccinimidyl) suberate. Accessible amine groups present on the N-termini of peptides react with NHS-esters to form amides. NHS-ester cross-linking reactions can be conducted in phosphate, bicarbonate/carbonate, HEPES and borate buffers. Other buffers can be used if they do not contain primary amines. The reaction of NHS-esters with primary amines should be conducted at a pH of between about 7 and about 9 and a temperature between about 4° C. and 30° C. for about 30 minutes to about 2 hours. The concentration of NHS-ester cross-linker can vary from about 0.1 to about 10 mM. NHS-esters are either hydrophilic or hydrophobic. Hydrophilic NHS-esters are reacted in aqueous solutions although DMSO may be included to achieve greater solubility. Hydrophobic NHS-esters are dissolved in a water miscible organic solvent and then added to the aqueous reaction mixture.

Sulfhydryl reactive cross-linkers include maleimides, alkyl halides, aryl halides and a-haloacyls which react with sulfhydryls to form thiol ether bonds and pyridyl disulfides which react with sulthydryls to produce mixed disulfides. Sulfhydryl groups on peptides and proteins can be generated by techniques known to those with skill in the art, e.g., by reduction of disulfide bonds or addition by reaction with primary amines using 2-iminothiolane. Examples of maleimide cross-linkers include succinimidyl 4-{N-maleimido-methyl) cyclohexane-1-carboxylate and m-maleimidobenzoyl-N-hydroxysuccinimide ester. Examples of haloacetal cross-linkers include N-succinimidyl (4-iodoacetal)aminobenzoate and sulfosuccinimidyl (4-iodoacetal) aminobenzoate. Examples of pyridyl disulfide cross-linkers include 1,4-Di-[3'-2'-pyridyldithio(propionamido)butane] and N-succinimidyl-3-(2-pyridyldithio)-propionate.

Carboxyl groups are cross-linked to primary amines or hydrazides by using carbodimides which result in formation of amide or hydrazone bonds. In this manner, carboxy-termini of peptides or proteins can be linked. Examples of carbodiimide cross-linkers include 1-ethyl-3-(3-dimethylaminopropyl)-carbodiimide hydrochloride and N, $N^1$-dicyclohexylcarbodiimide. Arylazide cross-linkers become reactive when exposed to ultraviolet radiation and form aryl nitrene. Examples of arylazide cross-linkers include azidobenzoyl hydrazide and N-5-azido-2 nitrobenzoyloxysuccinimide. Glyoxal cross linkers target the guanidyl portion of arginine. An example of a glyoxal cross-linker is p-azidophenyl glyoxal monohydrate.

Heterobifunctional cross-linkers which possess two or more different reactive groups are suitable for use herein. Examples include cross-linkers which are amine-reactive at one end and sulfhydryl-reactive at the other end such as 4-succinimidyl-oxycarbonyl-a-(2-pyridyldithio)-toluene, N-succinimidyl-3-(2-pyridyldithio)-propionate and the maleimide cross-linkers discussed above.

Attachment of surface reactive members to the polymeric fiber provides the fiber with the ability to form a covalent bond with the linking member upon exposure to the complementary surface reactive members on the linking member.

Attachment of tissue reactive members to the polymeric fiber provides the fiber with the ability to form covalent bonds with the biological tissue upon implantation, thus adhering the fiber to the tissue.

In one embodiment, a linking member is degradable by, e.g., hydrolysis or enzymatic action. In this manner, the fiber can be removable from the tissue and/or the linking member after a period of time. The degradable linkage may be, e.g., chelates or chemically or enzymatically hydrolyzable or absorbable. Illustrative chemically hydrolyzable degradable linkages include polymers, copolymers and oligomers of glycolide, dl-lactide, 1-lactide, caprolactone, dioxanone, and trimethylene carbonate. Illustrative enzymatically hydrolyzable biodegradable linkages include peptidic linkages cleavable by metalloproteinases and collagenases. Additional illustrative degradable linkages include polymers and copolymers of poly(hydroxy acid)s, poly(orthocarbonate)s, poly(anhydride)s, poly(lactone)s, poly(amino acid)s, poly(carbonate)s, poly(saccharide)s and poly(phosphonate)s. In certain embodiments, the degradable linkage may contain ester linkages. Some non-limiting examples include esters of succinic acid, glutaric acid, propionic acid, adipic acid, or amino acids, as well as carboxymethyl esters.

The polymeric fibers described herein may be cut to a desired length or shape, packaged in suture packaging or single or dual packages and sterilized by gamma or beta irradiation at 25-35 Kgy or by ethylene oxide.

Turning now to FIG. 1, polymeric fiber 15 includes surface reactive members, in this case azide groups 12. Linking members 20 including complimentary surface reactive members, in this case alkyne groups 14, and tissue reactive members 16, may be attached to fiber 15 upon interaction or contact of surface reactive members 12 with complimentary surface reactive members 14. As those skilled in the art will recognize, reaction times between the azide and alkyne members can be reduced from about 24 hours at room temperature to mere seconds at room temperature by the presence of transition metal ions, such as copper ions or upon exposure to ultraviolet light.

Figure 2:
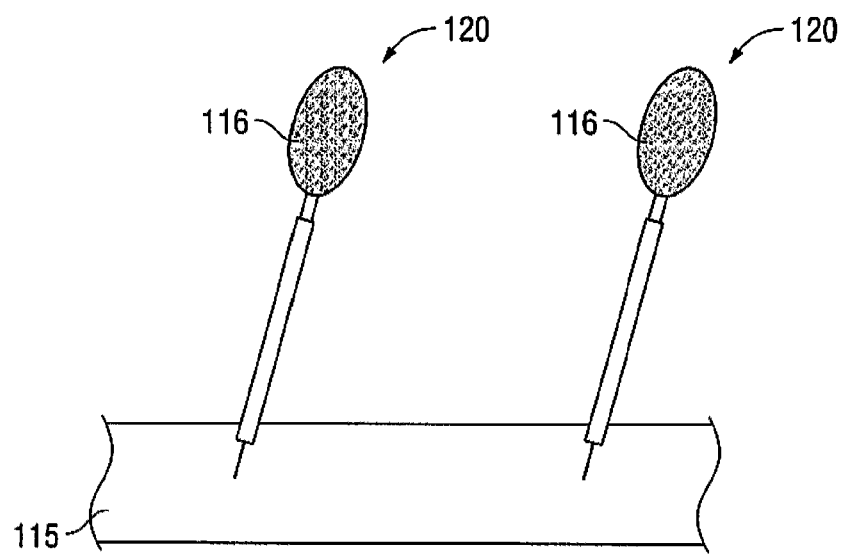
FIG. 2 schematically illustrates a fiber having a tissue reactive member covalently attached via a specific binding pair.

As depicted in FIG. 2, linking member 120 is attached to polymeric fiber 115. In addition, polymeric fiber 115 also includes pendant tissue reactive members 116 which are capable of interacting with biological tissue to covalently attach fiber 115 to the tissue following implantation. In embodiments wherein the surface reactive member is an alkyne and the complimentary surface reactive ember is an azide, the linking member may be attached to the fiber via a triazole (not shown).

Figure 3:
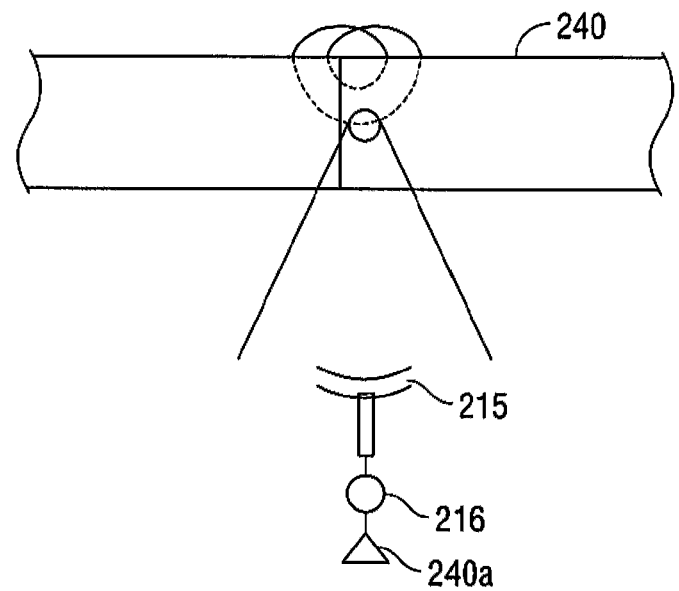
FIG. 3 schematically illustrates a fiber closing wound tissue in accordance with an embodiment described herein.

Unlike conventional wound closure devices, the polymeric fibers described herein may not need to form a knot or be crimped to maintain closure of the wound tissue. As shown in FIG. 3, fiber 215, i.e., a surgical suture, may be passed through approximated wound tissue 240 to close or seal wound tissue 240. Because pendant tissue reactive members 216 of fiber 215 form covalent bonds with at least portions of tissue 240a, polymeric fiber 215 may be able to maintain closure of wound tissue 240 without the need of forming a knot in fiber 215.

Figure 4:
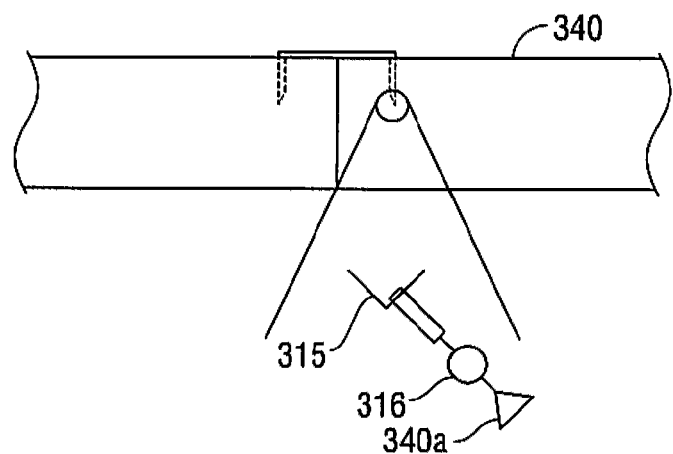
FIG. 4 schematically illustrates a fiber closing wound tissue in accordance with another embodiment described herein.

Similarly, in FIG. 4, fiber 315, i.e., a surgical staple, may be passed through approximated wound tissue 340 to close or seal wound tissue 340. Because pendant tissue reactive members 316 of fiber 315 form covalent bonds with at least portions of tissue 340a, polymeric fiber 315 may be able to maintain closure of wound tissue 340 without the need of crimping fiber 315.

It should be understood that variations can be made to the above embodiments that are with the purview of ordinary skill in the art. For example, other click chemistry reactions are suitable for use herein, e.g., Staudinger reaction of phosphines with alkyl azides. It is contemplated that the above-described cross-linkers may be applied to polymers which make up the fiber to bind reactive members or complementary reactive members thereto. Accordingly, those skilled in the art can envision modifications which are included within the scope of the claimed invention that are not expressly set forth herein.

What is claimed is:

1. A method for bonding a polymeric fiber to biological tissue comprising:
   providing a polymeric fiber having a plurality of surface reactive members of a specific binding pair attached on a surface of the fiber;
   attaching a plurality of linking members to the surface of the polymeric fiber, each linking member having at least one complimentary surface reactive member of the specific binding pair and at least one tissue reactive member, wherein the complimentary surface reactive member covalently attaches the linking member to the surface reactive member of the polymeric fiber via click chemistry and the tissue reactive member remains capable of covalently bonding to biological tissue; and
   contacting the polymeric fiber with the tissue, wherein upon contact of the tissue reactive members on the surface of the polymeric fiber with biological tissue, covalent bonds are formed between the tissue reactive members and the biological tissue, thus adhering the polymeric fiber to the biological tissue.

2. The method for bonding a polymeric fiber to biological tissue according to claim 1 wherein the surface reactive members and the complimentary surface reactive members of the specific binding pair bind to one another via a reaction selected from the group consisting of Huisgen cycloaddition reaction, a Diels-Alder reaction and a thiol-ene reaction.

3. The method for bonding a polymeric fiber to biological tissue according to claim 2 wherein the members of the specific binding pair are alkynes and azides.

4. The method for bonding a polymeric fiber to biological tissue according to claim 1 wherein the surface reactive member is an alkyne and the complementary surface reactive member is an azide.

5. The method for bonding a polymeric fiber to biological tissue according to claim 1 wherein the surface reactive member is an azide and the complementary surface reactive member is an alkyne.

6. The method for bonding a polymeric fiber to biological tissue according to claim 2 wherein the reaction is catalyzed by copper to activate an alkyne and an azide for [3+2] cycloaddition.

7. The method for bonding a polymeric fiber to biological tissue according to claim 2 wherein the reaction involves a cyclooctyne reagent and an azide for [3+2] cycloaddition.

8. The method for bonding a polymeric fiber to biological tissue according to claim 1 wherein the surface reactive member and the complimentary surface reactive member are thiols and alkenes.

9. The method for bonding a polymeric fiber to biological tissue according to claim 1 wherein the surface reactive member and the complimentary surface reactive member are dienes and alkenes.

10. The method for bonding a polymeric fiber to biological tissue according to claim 1 wherein the polymeric fiber comprises a monofilament suture.

11. The method for bonding a polymeric fiber to biological tissue according to claim 1 wherein the polymeric fiber comprises a multifilament suture.

12. The method for bonding a polymeric fiber to biological tissue according to claim 1 wherein the polymeric fiber comprises a surgical staple.

13. The method for bonding a polymeric fiber to biological tissue according to claim 1 wherein the polymeric fiber is used to form a surgical mesh.

14. The method for bonding a polymeric fiber to biological tissue according to claim 1 wherein the polymeric fiber is made of a polymer selected from the group consisting of polycarbonates, polyolefins, polymethacrylates, polystyrenes, polyamides, polyurethanes, polyethylene terephthalate, poly (lactic acid), poly (glycolic acid), poly (hydroxbutyrate), dioxanones (e.g., 1,4-dioxanone), .delta.-valerolactone, 1,dioxepanones (e.g., 1,4-dioxepan-2-one and 1,5-dioxepan-2-one), poly (phosphazine), polyesters, polyethylene glycol, polyethylene oxides, polyacrylamides, cellulose esters, fluoropolymers, vinyl polymers, silk, collagen, alginate, chitin, chitosan, hyaluronic acid, chondroitin sufate, polyhydroxyethylmethylacrylate, polyvinylpyrrolidone, polyvinyl alcohol, polyacrylic acid, polyacetate, polycaprolactone, polypropylene, glycerols, poly (amino acids), copoly (ether-esters), polyalkylene oxalates, polyamides, poly (iminocarbonates), polyalkylene oxalates, polyoxaesters, polyorthoesters, polyphosphazenes, polypeptides and copolymers, block copolymers, homoploymers, blends and combinations thereof.

15. The method for bonding a polymeric fiber to biological tissue according to claim 1 wherein the tissue reactive member is an electrophile.

16. The method for bonding a polymeric fiber to biological tissue according to claim 1 wherein the tissue reactive member is a nucleophile.

17. The method for bonding a polymeric fiber to biological tissue according to claim 1 wherein the polymeric fiber comprises at least one barb.

18. A polymeric fiber comprising: a surface having a plurality of surface reactive members of a specific binding pair; and a plurality of linking members, each linking member including at least one complimentary surface reactive member of the specific binding pair, and at least one tissue reactive member, wherein the surface reactive members and the complimentary surface reactive members are covalently bonded, adhering the tissue reactive members to the surface of the fiber.

19. The polymeric fiber according to claim 18 wherein the surface reactive members and the complimentary surface reactive members of the specific binding pair are covalently bonded to one another via a reaction selected from the group consisting of Huisgen cycloaddition reaction, a Diels-Alder reaction and a thiol-ene reaction.

20. The polymeric fiber according to claim 18 wherein the surface reactive members and the complimentary surface reactive members of the specific binding pair are alkynes and azides.

21. The polymeric fiber according to claim 18 wherein the surface reactive members are alkynes and the complementary surface reactive members are azides.

22. The polymeric fiber according to claim 18 wherein the surface reactive members are azides and the complementary surface reactive members are alkynes.

23. The polymeric fiber according to claim 19 wherein the reaction is catalyzed by copper to activate an alkyne and an azide for [3+2] cycloaddition.

24. The polymeric fiber according to claim 19 wherein the reaction involves a cyclooctyne reagent and an azide for [3+2] cycloaddition.

25. The polymeric fiber according to claim 18 wherein the surface reactive members and the complimentary surface reactive members are thiols and alkenes.

26. The polymeric fiber according to claim 18 wherein the surface reactive members and the complimentary surface reactive members are dienes and alkenes.

27. The polymeric fiber according to claim 18 wherein the polymeric fiber comprises a monofilament suture.

28. The polymeric fiber according to claim 18 wherein the polymeric fiber comprises a multifilament suture.

29. The polymeric fiber according to claim 18 wherein the polymeric fiber comprises a surgical staple.

30. The polymeric fiber according to claim 18 wherein the polymeric fiber is used to form a surgical mesh.

31. The polymeric fiber according to claim 18 wherein the polymeric fiber is made of a polymer selected from the group consisting of polycarbonates, polyolefins, polymethacrylates, polystyrenes, polyamides, polyurethanes, polyethylene terephthalate, poly (lactic acid), poly (glycolic acid), poly (hydroxbutyrate), dioxanones (e.g., 1,4-dioxanone), .delta.-valerolactone, 1,dioxepanones (e.g., 1,4-dioxepan-2-one and 1,5-dioxepan-2-one), poly (phosphazine), polyesters, polyethylene glycol, polyethylene oxides, polyacrylamides, cellulose esters, fluoropolymers, vinyl polymers, silk, collagen, alginate, chitin, chitosan, hyaluronic acid, chondroitin sufate, polyhydroxyethylmethylacrylate, polyvinylpyrrolidone, polyvinyl alcohol, polyacrylic acid, polyacetate, polycaprolactone, polypropylene, glycerols, poly (amino acids), copoly (ether-esters), polyalkylene oxalates, polyamides, poly (iminocarbonates), polyalkylene oxalates, polyoxaesters, polyorthoesters, polyphosphazenes, polypeptides and copolymers, block copolymers, homoploymers, blends and combinations thereof.

32. The polymeric fiber according to claim 18 wherein the tissue reactive members are electrophiles.

33. The polymeric fiber according to claim 18 wherein the tissue reactive members nucleophiles.

34. The polymeric fiber according to claim 18 wherein the polymeric fiber comprises at least one barb.

* * * * *